(12) United States Patent
Thornton

(10) Patent No.: US 8,020,276 B2
(45) Date of Patent: Sep. 20, 2011

(54) SYSTEM AND METHOD FOR CUSTOM-ORIENTING A MEDICAL MASK TO AN ORAL APPLIANCE

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 964 days.

(21) Appl. No.: 11/947,291

(22) Filed: Nov. 29, 2007

(65) Prior Publication Data

US 2008/0127984 A1    Jun. 5, 2008

Related U.S. Application Data

(60) Provisional application No. 60/867,937, filed on Nov. 30, 2006.

(51) Int. Cl.
*B23Q 3/00*    (2006.01)
*A62B 18/02*   (2006.01)

(52) U.S. Cl. ..................... 29/464; 128/206.21

(58) Field of Classification Search ............. 29/464, 29/467, 469, 896.1, 527.1, 450, 428; 128/206.21, 128/206.24, 205.25, 206.28, 201.22, 201.29
See application file for complete search history.

(56) References Cited

U.S. PATENT DOCUMENTS

| 339,334 A | 4/1886 | Searle |
|---|---|---|
| 690,663 A | 1/1902 | Pratt |
| 746,869 A | 12/1903 | Moulton |
| 774,446 A | 11/1904 | Moulton |
| 781,516 A | 1/1905 | Guthrie, Jr. |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |

(Continued)

FOREIGN PATENT DOCUMENTS

DE    156627    12/1904

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner* — John C Hong
(74) *Attorney, Agent, or Firm* — Baker Botts L.L.P.

(57) ABSTRACT

In one embodiment, a medical mask includes a body and an orientation structure. The body includes a first polymer, is configured to cover portions of a user's face comprising the user's mouth and at least portions of the user's nose comprising the nostrils, and is further configured to contact the user's face surrounding the covered portions of the user's face to substantially prevent gas from escaping between the body and the contacted portions of the user's face. The orientation structure is configured to receive an oral appliance post to establish and maintain a custom orientation between the medical mask and the oral appliance post and the orientation structure includes a deformable material which includes a second polymer capable of transitioning between deformable and non-deformable states.

20 Claims, 6 Drawing Sheets

U.S. PATENT DOCUMENTS

| | | | |
|---|---|---|---|
| 1,649,664 A | 11/1927 | Carter | |
| 1,674,336 A | 6/1928 | King | |
| 1,675,202 A | 6/1928 | Warne | |
| 1,679,748 A | 8/1928 | Stratton | |
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,671,446 A | 3/1954 | Mann | 128/163 |
| 2,712,160 A | 7/1955 | Sterczek | 18/55.05 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 2,917,045 A | 12/1959 | Schildknecht et al. | 128/141 |
| 2,977,636 A | 4/1961 | McGuire | 18/58.7 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,521 A | 5/1967 | Weisberg | 32/32 |
| 3,330,274 A | 7/1967 | Bennett | 128/146.7 |
| 3,360,860 A | 1/1968 | Roland | 32/17 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,695,265 A | 10/1972 | Brevik | 128/146.2 |
| 3,845,768 A | 11/1974 | Garrahan | 128/142.7 |
| 3,854,208 A | 12/1974 | Arant | 32/19 |
| 3,864,832 A | 2/1975 | Carlson | 32/40 R |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,050,457 A | 9/1977 | Davidson | 128/145.5 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205.24 |
| 4,289,127 A | 9/1981 | Nelson | 128/207.14 |
| 4,294,243 A | 10/1981 | Ernsting et al. | 128/201.18 |
| 4,304,227 A | 12/1981 | Samelson | 128/136 |
| 4,345,592 A | 8/1982 | Giorgini et al. | 128/204.26 |
| 4,345,593 A | 8/1982 | Sullivan | 128/204.26 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202.27 |
| 4,397,701 A | 8/1983 | Johnson et al. | 156/62 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A | 6/1984 | Saumell | 264/154 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,605 A | 8/1989 | Levy | 128/203.11 |
| 4,858,606 A | 8/1989 | Hamlin | 128/204.29 |
| 4,862,903 A | 9/1989 | Campbell | 128/861 |
| 4,870,962 A | 10/1989 | Sitnik | 128/205.13 |
| 4,886,056 A | 12/1989 | Simpson | 128/201.25 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,941,212 A | 7/1990 | Liff | 2/206 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,062,421 A | 11/1991 | Burns et al. | 128/205.27 |
| 5,064,371 A | 11/1991 | Smeltzer | 433/37 |
| 5,065,756 A | 11/1991 | Rapoport | 128/204.18 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204.25 |
| 5,213,498 A | 5/1993 | Pelerin | 433/37 |
| 5,233,978 A | 8/1993 | Callaway | 128/205.25 |
| 5,243,971 A | 9/1993 | Sullivan et al. | 128/205.25 |
| 5,245,995 A | 9/1993 | Sullivan et al. | 128/204.23 |
| 5,267,557 A | 12/1993 | Her-Mou | 128/206.21 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,392,773 A | 2/1995 | Bertrand | 128/206.11 |
| 5,409,017 A | 4/1995 | Lowe | 128/848 |
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204.23 |
| 5,477,850 A | 12/1995 | Zegler et al. | 128/202.11 |
| 5,503,146 A | 4/1996 | Froehlich et al. | 128/204.23 |
| 5,503,552 A | 4/1996 | Diesso | 433/37 |
| 5,517,983 A | 5/1996 | Deighan et al. | 128/204.23 |
| 5,537,994 A | 7/1996 | Thornton | 128/204.18 |
| 5,537,999 A | 7/1996 | Dearman et al. | 128/205.25 |
| 5,538,000 A | 7/1996 | Rudolph | 128/205.25 |
| 5,538,014 A | 7/1996 | Wilson et al. | 128/863 |
| 5,540,223 A | 7/1996 | Starr et al. | 128/205.25 |
| 5,551,419 A | 9/1996 | Froehlich et al. | 128/204.23 |
| 5,551,872 A | 9/1996 | Mena | 433/37 |

| | | | |
|---|---|---|---|
| 5,558,090 A | 9/1996 | James | 128/207.18 |
| RE35,339 E | 10/1996 | Rapoport | 128/204.18 |
| 5,560,354 A | 10/1996 | Berthon-Jones et al. | 128/205.25 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,592,935 A | 1/1997 | Elstran et al. | 128/205.29 |
| 5,611,485 A | 3/1997 | Davis | 239/8 |
| 5,657,751 A | 8/1997 | Karr, Jr. | 128/205.18 |
| 5,657,752 A | 8/1997 | Landis et al. | 128/207.13 |
| 5,662,101 A | 9/1997 | Ogden et al. | 128/205.25 |
| 5,676,133 A | 10/1997 | Hickle et al. | 128/205.12 |
| 5,678,567 A | 10/1997 | Thornton et al. | 128/848 |
| 5,681,164 A | 10/1997 | Bass | 433/6 |
| 5,687,715 A | 11/1997 | Landis et al. | 128/207.18 |
| 5,713,349 A | 2/1998 | Keaney | 128/204.23 |
| 5,718,244 A | 2/1998 | Thornton | 128/864 |
| 5,718,500 A | 2/1998 | Vinci guera et al. | 2/431 |
| 5,720,280 A | 2/1998 | Elstran et al. | 128/205.25 |
| 5,720,302 A | 2/1998 | Belfer | 128/848 |
| 5,724,965 A | 3/1998 | Handke et al. | 128/207.13 |
| 5,746,201 A | 5/1998 | Kidd | 128/206.24 |
| 5,752,510 A | 5/1998 | Goldstein | 128/207.18 |
| 5,755,219 A | 5/1998 | Thornton | 128/201.18 |
| 5,807,100 A | 9/1998 | Thornton | 433/48 |
| 5,810,749 A | 9/1998 | Maas | 602/6 |
| 5,829,441 A | 11/1998 | Kidd et al. | 128/848 |
| 5,832,918 A | 11/1998 | Pantino | 128/205.25 |
| 5,846,082 A | 12/1998 | Thornton | 433/215 |
| 5,887,587 A | 3/1999 | Groenke | 128/207.13 |
| 5,891,372 A | 4/1999 | Besset et al. | 264/46.5 |
| 5,954,048 A | 9/1999 | Thornton | 128/201.18 |
| 5,983,892 A | 11/1999 | Thornton | 128/201.26 |
| 5,988,166 A | 11/1999 | Hayek | 128/205.26 |
| 6,012,455 A | 1/2000 | Goldstein | 128/207.18 |
| 6,083,442 A | 7/2000 | Gabilly | 264/163 |
| 6,109,265 A | 8/2000 | Frantz et al. | 128/848 |
| 6,119,694 A | 9/2000 | Correa et al. | 128/207.13 |
| 6,123,071 A | 9/2000 | Berthon-Jones et al. | 128/204.18 |
| 6,155,262 A | 12/2000 | Thornton et al. | 128/859 |
| 6,209,542 B1 | 4/2001 | Thornton | 128/206.29 |
| 6,247,926 B1 | 6/2001 | Thornton | 433/48 |
| 6,263,871 B1 | 7/2001 | Brown et al. | 128/200.29 |
| D448,473 S | 9/2001 | Barnett et al. | D24/110.1 |
| 6,305,376 B1 | 10/2001 | Thornton | 128/848 |
| 6,318,997 B1 | 11/2001 | Mayweather | 433/45 |
| 6,325,064 B1 | 12/2001 | Thornton | 128/204.18 |
| 6,374,824 B1 | 4/2002 | Thornton | 128/201.26 |
| 6,405,729 B1 | 6/2002 | Thornton | 128/848 |
| 6,412,488 B1 | 7/2002 | Barnett et al. | 128/207.13 |
| 6,464,924 B1 | 10/2002 | Thornton | 264/331.12 |
| 6,494,206 B1 | 12/2002 | Bergamaschi et al. | 128/206.24 |
| 6,516,805 B1 | 2/2003 | Thornton | 128/848 |
| 6,536,439 B1 | 3/2003 | Palmisano | |
| 6,571,798 B1 | 6/2003 | Thornton | 128/206.21 |
| 6,604,527 B1 | 8/2003 | Palmisano | |
| 6,645,413 B2 | 11/2003 | Jacobs | 264/222 |
| 6,675,802 B1 | 1/2004 | Thornton | 128/206.29 |
| 6,758,212 B2* | 7/2004 | Swann | 128/201.25 |
| 6,769,910 B1 | 8/2004 | Pantino | |
| 6,845,774 B2 | 1/2005 | Gaskell | 128/848 |
| 6,857,428 B2 | 2/2005 | Thornton | 128/206.21 |
| 6,877,513 B2 | 4/2005 | Scarberry et al. | 128/848 |
| 7,077,138 B2 | 7/2006 | Bateman et al. | 128/206.14 |
| 7,174,895 B2 | 2/2007 | Thornton et al. | 128/848 |
| 7,832,403 B2 | 11/2010 | Halstrom et al. | |
| 7,909,035 B2* | 3/2011 | Thornton | 128/206.21 |
| 2002/0129818 A1 | 9/2002 | Morgan et al. | 128/206.26 |
| 2004/0226563 A1* | 11/2004 | Xu et al. | 128/206.21 |
| 2004/0237965 A1 | 12/2004 | Bibi et al. | 128/206.29 |
| 2005/0016544 A1 | 1/2005 | Thornton | 128/207.18 |
| 2006/0005837 A1 | 1/2006 | Thornton | 128/205.25 |
| 2006/0124131 A1 | 6/2006 | Chandran et al. | 128/206.28 |
| 2007/0006879 A1 | 1/2007 | Thornton | 128/203.29 |
| 2007/0125388 A1 | 6/2007 | Thornton et al. | 128/848 |
| 2007/0235037 A1 | 10/2007 | Thornton | 128/848 |
| 2008/0006273 A1 | 1/2008 | Thornton | 128/206.21 |
| 2008/0006274 A1 | 1/2008 | Thornton | 128/206.21 |
| 2008/0032256 A1 | 2/2008 | Thornton | 433/57 |
| 2008/0060648 A1 | 3/2008 | Thornton et al. | 128/205.25 |

FOREIGN PATENT DOCUMENTS

| | | |
|---|---|---|
| DE | 2 320 501 | 11/1974 |
| DE | 35 43 931 A1 | 6/1987 |
| DE | 37 07 952 A1 | 9/1988 |
| DE | 37 19 009 A1 | 12/1988 |
| DE | 29506512.5 | 7/1995 |
| DE | 44 38 512 A1 | 5/1996 |
| DE | 195 24 534 C1 | 6/1996 |
| DE | 198 46 686 A1 | 7/1999 |
| EP | 0 312 368 A1 | 4/1989 |
| EP | 0 359 135 A1 | 3/1990 |
| FR | 2 658 725 A1 | 8/1991 |
| FR | 2 731 624 A1 | 9/1996 |
| FR | 2731624 | 9/1996 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/20924 | 5/1998 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Lboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 4 pages.

Great Lakes Orthodontics, Ltd.; *Nocturnal Airway Patency Applicance*; 2 pages.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

CPAP-PRO— *Introducing A New Comfort Level for CPAP Users* brochure, 2 pages.

"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.

PCT Notification of Transmittal of The International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT Notification of Transmittal of the International Search Report and the Written Opinion of the International Searching Authority, or the Declaration, PCT/US 06/26622, 10 pages, Mailing Date Feb. 21, 2007.

PCT, Notification of Transmittal of the International Search Report and the Written Opinion of the International Searching Authority, or the Declaration, PCT/US07/02736, 10 pages, Date Mailed Oct. 26, 2007.

Patent Pending U.S. Appl. No. 11/278,918 entitled *Oral Appliance for Treating a Breathing Condition*, by W. Keith Thornton, 42 total pages, filed Apr. 6, 2006.

Patent Pending U.S. Appl No. 11/428,933 entitled *Multi-Chamber Mask and Method of Forming the Same*, by W. Keith Thornton, 23 total pages, filed Jul. 6, 2006.

European Patent Office Communication, Application No. 03 809 555.0-1257, Applicant: W. Keith Thornton, 4 pages, dated Aug. 7, 2009.

* cited by examiner

SYSTEM AND METHOD FOR CUSTOM-ORIENTING A MEDICAL MASK TO AN ORAL APPLIANCE

RELATED APPLICATION

This application claims the benefit under 35 U.S.C. §119 (e) of U.S. Provisional Application Ser. No. 60/867,937 filed Nov. 30, 2006.

TECHNICAL FIELD

This invention relates generally to masks for use in medical and other clinical applications, and more particularly to a system and method for custom-orienting a medical mask to an oral appliance.

BACKGROUND

Many people experience breathing problems on a recurring basis, which often result in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included face masks, nose masks, or nasal inserts that help deliver air to the user's nose at positive pressure. These devices help force open the user's breathing passage and thereby improve the user's breathing. However, previous devices have often provided an inadequate fit and thus have caused discomfort for users and failed to adequately prevent leakage.

OVERVIEW

According to one embodiment, a medical mask includes a body and an orientation structure. The body includes a first polymer, is configured to cover portions of a user's face comprising the user's mouth and at least portions of the user's nose comprising the nostrils, and is further configured to contact the user's face surrounding the covered portions of the user's face to substantially prevent gas from escaping between the body and the contacted portions of the user's face. The orientation structure is configured to receive an oral appliance post to establish and maintain a custom orientation between the medical mask and the oral appliance post and the orientation structure includes a deformable material which includes a second polymer capable of transitioning between deformable and non-deformable states.

According to another embodiment, a method of forming a custom-oriented medical mask having a body and an orientation structure includes transitioning a deformable material for the orientation structure of the medical mask from a first non-deformable state to a deformable state; positioning in a user's mouth an oral appliance having a post, such that the oral appliance receives the user's teeth and the post of the oral appliance projects out of the user's mouth; positioning the medical mask over the user's face, such that the body of the medical mask covers portions of the user's face including at least the user's mouth and a portion of the user's nose surrounding the user's nostrils, the body of the medical mask contacts the user's face surrounding the covered portions of the user's face and substantially prevents gas from escaping between the body and the contacted portions of the user's face, and the post of the oral appliance is received in the orientation structure of the medical mask to establish a custom orientation between the medical mask and the post of the oral appliance; and, while the post of the oral appliance is received in the orientation structure of the medical mask, allowing the deformable material to transition from the deformable state to a second non-deformable state, such that the custom orientation between the medical mask and the post of the oral appliance is maintained.

According to another embodiment, a medical mask includes a body, an orientation structure, and a fitting. The body includes a non-thermoplastic polymer, is configured to cover portions of a user's face comprising the user's mouth and at least portions of the user's nose comprising the nostrils, and is further configured to contact the user's face surrounding the covered portions of the user's face to substantially prevent gas from escaping between the body and the contacted portions of the user's face. The orientation structure is configured to establish and maintain a custom orientation between the medical mask and a post of an oral appliance. The orientation structure includes a thermoplastic polymer and a locking mechanism coupled to the thermoplastic polymer and configured to receive and secure a post of an oral appliance. The fitting is configured to couple the medical mask to a clinical gas delivery system.

Certain embodiments may provide one or more technical advantages. Certain embodiments may provide a non-custom medical mask that may be customized to conform substantially optimally to a user's unique facial features. Certain embodiments may provide a medical mask that may couple to an oral appliance to provide an improved fit based on a custom orientation between a user's unique facial features and the user's teeth. Certain embodiments may provide a method for use in forming, modifying, or fitting a non-custom medical mask so that it can maintain a custom orientation between a user's unique facial features and the user's teeth to ensure that the medical mask has an optimal fit, customized for the user. Certain embodiments may provide improved fit, increased comfort, reduced leakage, and improved performance, whether for treating sleep disordered breathing, administering anesthesia, or any other suitable purpose for which the medical mask is used. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which.

DESCRIPTION OF EXAMPLE EMBODIMENTS

Figure 1A:
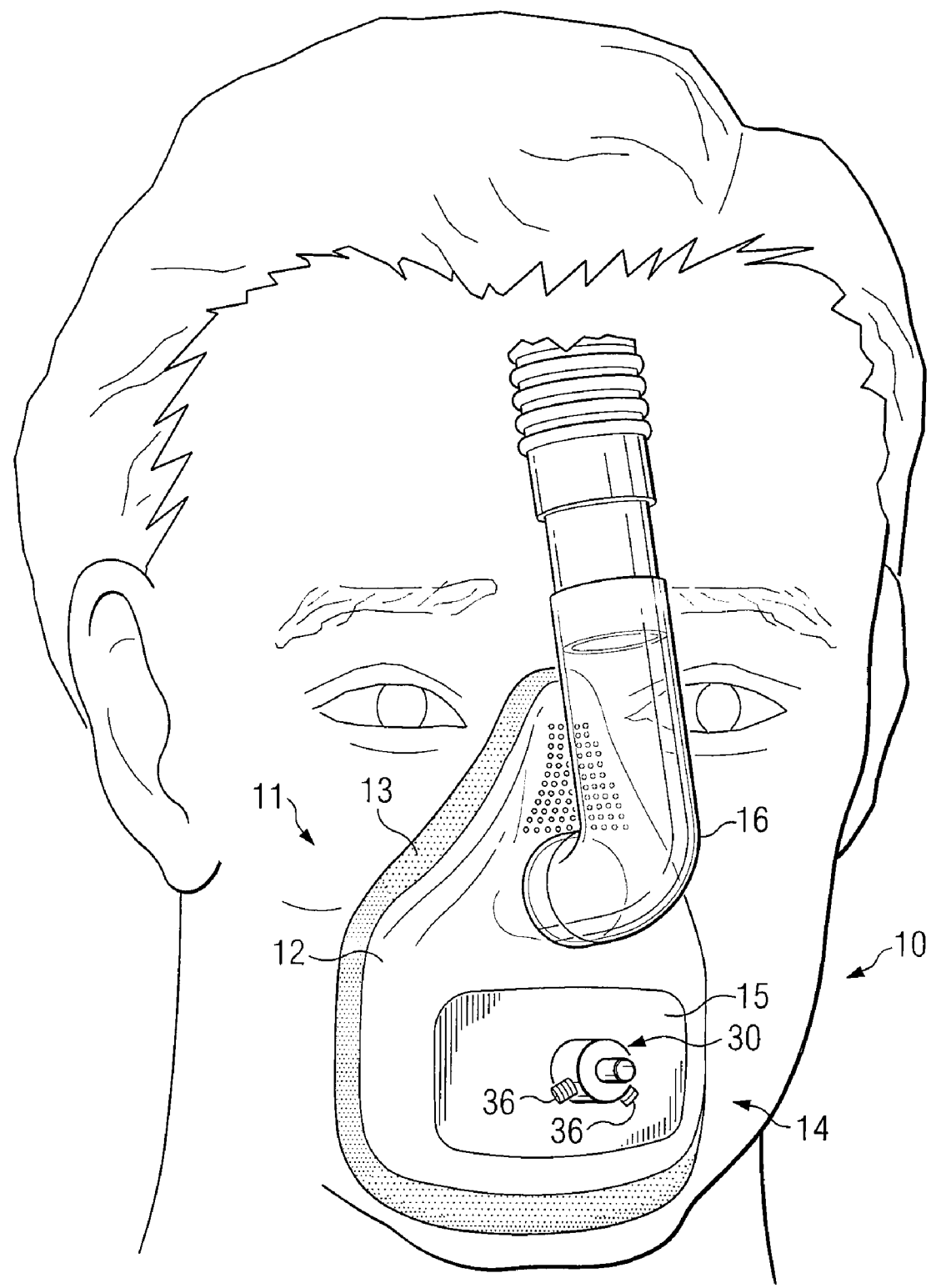
FIGS. 1A and 1B illustrate an example medical mask.
Figure 1B:
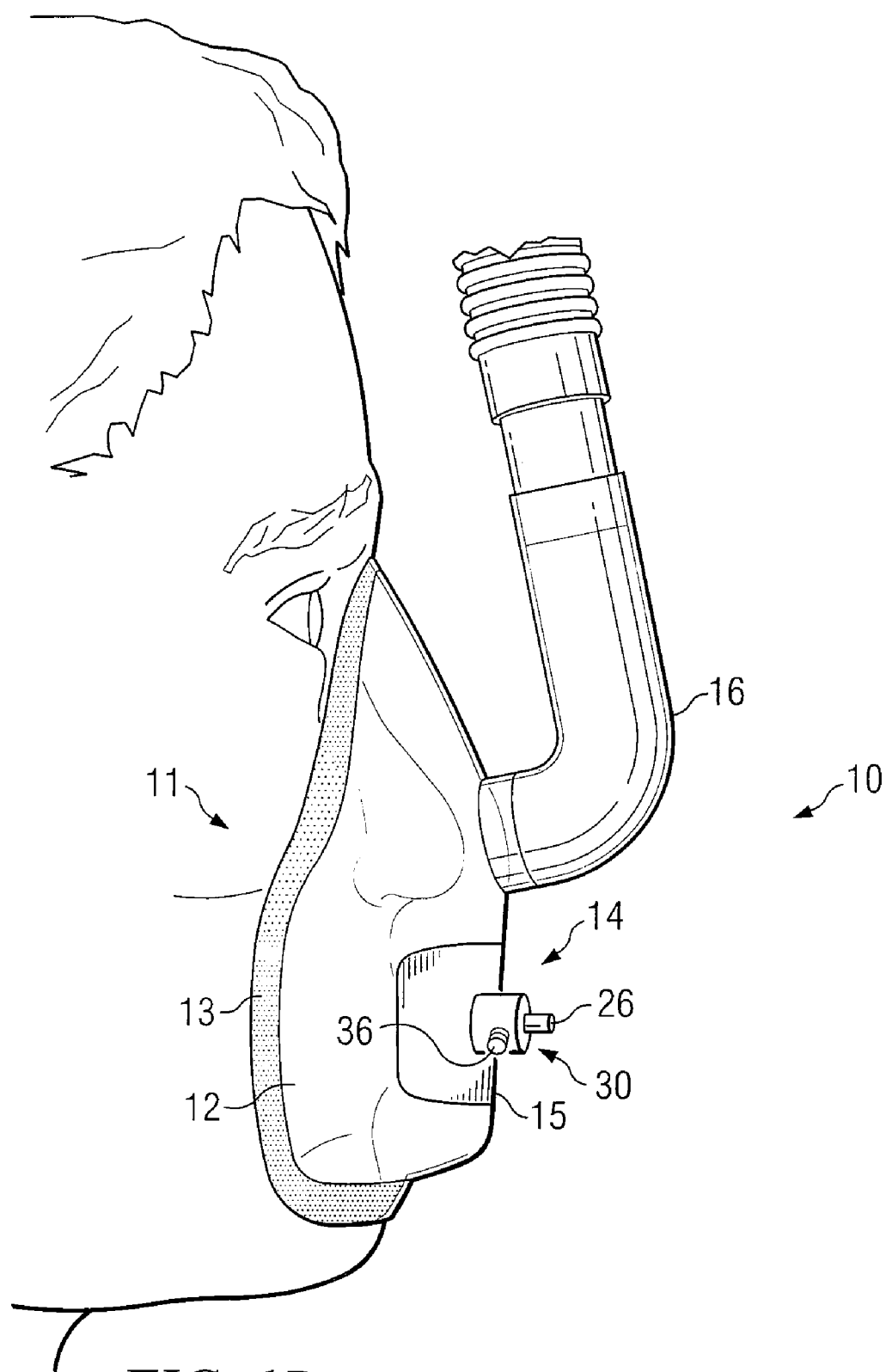

FIGS. 1A and 1B illustrate an example embodiment of medical mask 10. Medical mask 10 includes body 11 and orientation structure 14. In certain embodiments, medical mask 10 also includes fitting 16. In operation, medical mask 10 is custom-oriented to an oral appliance, such that when a user wears medical mask 10 with the oral appliance, medical mask 10 may be coupled to the oral appliance and the custom orientation between the medical mask and the oral appliance may be maintained throughout each use and between repeated uses. In certain embodiments, as a result of this custom-orientation, medical mask 10 provides an improved fit, increased comfort, reduced leakage, and improved performance, whether for treating sleep disordered breathing, administering anesthesia, or any other suitable purpose for which medical mask 10 is used.

Body 11 is configured to cover and seal around at least a portion of a user's face including the user's mouth and at least portions of the user's nose, including the nostrils. In certain embodiments, body 11 is configured to cover only the soft cartilaginous portions of the user's nose and portions of the user's face to the sides of and below the soft cartilaginous portions of the user's nose, but not to cover the hard bony portions of the nose generally above the soft cartilaginous portions of the nose. In alternative embodiments, body 11 may be configured to cover the user's entire nose and portions of the user's face to the sides of and below the user's nose, including the user's mouth. In certain embodiments, body 11 is configured to direct a flow of gas to the user's mouth and/or nostrils.

Body 11 may be formed from a single sheet of material or may include multiple components formed from various materials. In certain embodiments, body 11 includes shell 12 and sealing portion 13. In embodiments of body 11 including sealing portion 13, sealing portion 13 may allow medical mask 10 to conform to the unique facial features of a wide variety of users. Shell 12 represents the portion of body 11 configured to cover portions of the user's face and to direct a flow of gas to the user's mouth and/or nostrils. In certain embodiments, shell 12 is formed from one or more substantially rigid materials to allow shell 12 to retain a substantially fixed shape. All or a portion of shell 12 may be formed from a polymer. For example, shell 12 may be formed from a thermosetting polymer, a thermoplastic polymer, or a light curable polymer. Sealing portion 13 represents the portion of body 11 configured to contact the user's face to substantially prevent gas from escaping between shell 12 and the contacted portions of the user's face. In certain embodiments, sealing portion 13 may include a flexible gasket located at the periphery of shell 12 to provide an airtight seal between shell 12 and the user's face. Sealing portion may be formed from any appropriate flexible material, such as plastic, rubber, or silicone. In certain embodiments, shell 12 may be used with different sealing portions 13 depending on the size and shape of the user's face.

Fitting 16 couples to body 11 and directs a flow of gas into a chamber, such as a chamber created between body 11 and a user's face when medical mask 10 is worn. Fitting 16 may include any suitable structure to connect medical mask 10 to a suitable clinical gas delivery system. For example, fitting 16 may represent an acrylic, male-type hose connector that couples to an opening in body 11. As another example, fitting 16 may represent a gasket surrounding an opening into body 11. Fitting 16 may include a structure configured to connect custom medical mask 10 to one or more hoses. A suitable clinical gas delivery system may be a Continuous Positive Air Pressure (CPAP) system, a Bilevel Positive Air Pressure (Bi-PAP) system, or other system configured to deliver air, oxygen, anesthetic, or other gases to a user wearing medical mask 10.

Body 11 may be custom-formed or custom-fitted to a particular user's unique facial structure. As an example, body 11 may be formed at least in part using one or more techniques described in U.S. Pat. No. 6,857,428. Alternatively, body 11 may represent, include, or be formed from a non-custom mask. As an example, body 11 may be formed from a FLEXI-FIT face mask available from FISHER & PAYKEL HEALTHCARE of New Zealand.

Orientation structure 14 represents one or more structures configured to couple medical mask 10 to an oral appliance and to establish and maintain a custom orientation between medical mask 10 and the oral appliance. A description of an example oral appliance for use with medical mask 10 is provided below with reference to FIG. 4. Through the use of orientation structure 14, medical mask 10 may be custom-oriented for a particular user such that each time the particular user wears medical mask 10, the custom-orientation between medical mask 10 and the particular user's unique facial features may be maintained. In certain embodiments, orientation structure 14 maintains medical mask 10 in a position to provide an optimal seal between medical mask 10 and the particular user's face.

Figure 2:
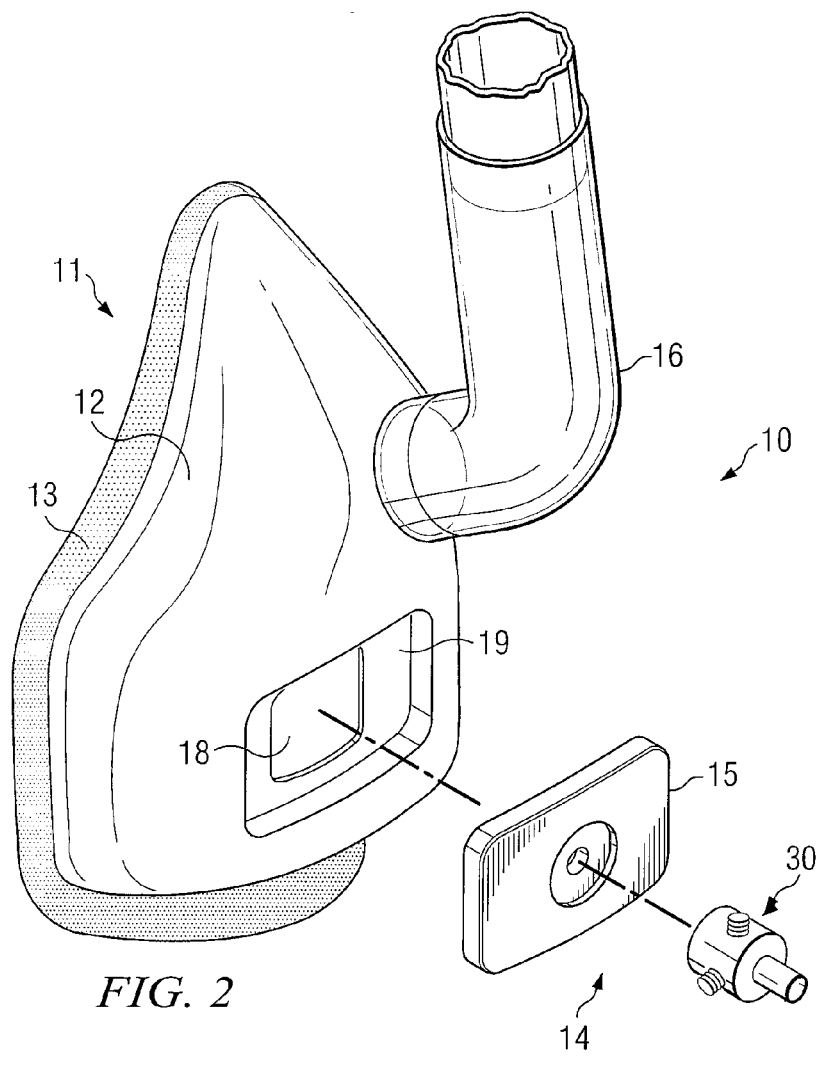
FIG. 2 illustrates an exploded view of an example medical mask.

FIG. 2 illustrates an exploded view of an example medical mask 10, showing body 11 separate from example components of orientation structure 14. In the embodiment shown, orientation structure 14 includes deformable material 15 and locking mechanism 30, such that deformable material 15 and locking mechanism 30 operate together to establish and maintain a custom orientation between medical mask 10 and an oral appliance. For example, while an oral appliance is positioned in a user's mouth and medical mask 10 is positioned over the user's face, a post of the oral appliance may project through opening 18 and be received by orientation structure 14. In this example, the post may project through deformable material 15 and be received and secured by locking mechanism 30. Descriptions of example locking mechanisms 30 are included below in relation to FIGS. 5A-5C. In certain embodiments, deformable material 15 may be placed in a deformable state such that orientation structure 14 deforms to establish a custom orientation between medical mask 10 and the oral appliance. In these embodiments, after deformable material 15 transitions to a non-deformable state, the custom orientation between medical mask 10 and the oral appliance may be maintained throughout each use and between repeated uses.

In certain embodiments, deformable material 15 includes a suitable thermoplastic polymer and suitable fillers, stabilizers, coloring agents, antioxidants, antimicrobial agents, and/or other materials. Alternatively, in certain embodiments, deformable material 15 may include a thermosetting or light curing material. For example, deformable material 15 may include the light curing material sold under the name TRIAD by DENTSPLY INTERNATIONAL INC. Such materials are known in various contexts to those skilled in the art.

In a particular embodiment, deformable material 15 includes, possibly in addition to one or more other materials, one or more of the thermoplastic polycaprolactone polymers or other aliphatic polyesters described in U.S. Pat. Nos. 4,784,123 and 5,112,225 and product literature of UNION CARBIDE CORPORATION. One or more polycaprolactone polymers may have the formula:

(1)

where R is an aliphatic hydrocarbon and n may range between approximately 300 to approximately 650. However, the present invention contemplates using any suitable polycaprolactone polymer.

For example, deformable material 15 may include one or more of the TONE P-700, TONE P-767, or TONE P-787 polycaprolactone polymers manufactured by UNION CARBIDE CORPORATION, singly or in any combination. In a particular example, deformable material 15 may include approximately thirty parts by volume of TONE P-700 and sixty parts by volume of TONE P-767, together with approximately ten parts by volume of one or more other polymers, depending upon the application and particular needs.

TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

$$\text{HO—R—OH} \quad (2)$$

where R is an aliphatic hydrocarbon. In general, polycaprolactone polymers may display desirable dimensional stability and thermoplasticity during cooling, biocompatibility, and a variety of other characteristics making them suitable for use in forming embodiments of medical mask 10.

In certain embodiments, deformable material 15 may be applied to body 11 in the form of a thin sheet of material. For example, deformable material 15 may have a thickness in the rage between approximately 0.1 and approximately 0.3 inches. In a particular embodiment, deformable material 15 may have a thickness of approximately 0.125 inches. Although deformable material 15 may have any appropriate shape, in certain embodiments deformable material 15 may be substantially circular, substantially square, or substantially rectangular with rounded corners. As shown in FIG. 2, in certain embodiments, deformable material 15 may include an opening configured to receive a post of an oral appliance and a countersink configured to receive a portion of locking mechanism 30. In certain embodiments, deformable material 15 may be applied to body 11 in a deformable state to conform to the shape of body 11 and/or locking mechanism 30.

In the embodiment shown in FIG. 2, body 11 includes opening 18 and tray 19. Opening 18 is configured to be positioned anterior to a user's mouth when the user is wearing medical mask 10 and to provide a passage through which a post of an oral appliance may be received. For example, although opening 18 may have any appropriate size or shape, in certain embodiments opening 18 may be a substantially circular, square, or rectangular opening with a width in the range between approximately 0.5 and approximately 1.5 inches, and more particularly a substantially square opening with a width of approximately 1.0 inches. The size and shape of opening 18 may affect the range of custom orientations available with medical mask 10. For example, if a 0.25 inch diameter oral appliance post extends through a 1.25 inch diameter circular opening 18 in body 11, then medical mask 10 may be vertically and horizontally adjustable within a 1.0 inch diameter circular region.

Tray 19 represents a portion of body 11 configured to receive and surround at least a portion of orientation structure 14. For example, tray 19 may be a depression in body 11 configured to receive and surround deformable material 15. In certain embodiments, the depth of tray 19 may be substantially equal to the thickness of deformable material 15. In certain embodiments, the shape of tray 19 and of deformable material 15 may be substantially the same such that, when deformable material 15 is received and surrounded by tray 19, tray 19 defines a substantially fixed position for deformable material 15 relative to body 11.

Figure 3:
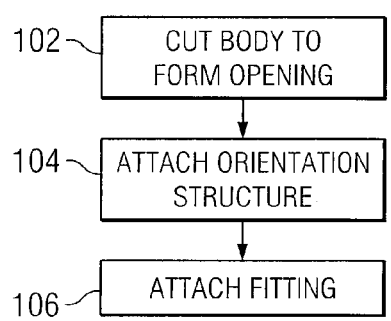
FIG. 3 illustrates an example method for forming a medical mask.

FIG. 3 illustrates an example method 100 for forming medical mask 10. At step 102, a hole may be cut in body 11 to form opening 18. For example, using a drill press or other rotary cutting tool, a hole may be cut generally in the location shown in FIG. 2 for opening 18. In alternative embodiments, rather than cutting a hole in body 11 to form opening 18, body 11 may be initially formed having opening 18.

At step 104, orientation structure 14 may be applied to body 11, with or without tray 19. For example, orientation structure 14 may represent a deformable material 15, alone or together with one or more additional components, such as locking mechanism 30. Orientation structure 14 may be applied by positioning deformable material 15 on body 11 proximate to opening 18. In embodiments including additional components, such as locking mechanism 30, the additional components may be appropriately positioned prior to or subsequent to positioning deformable material 15. Deformable material 15 may be applied to body 11 after body 11 has been positioned over a user's face. Orientation structure 14 may then be coupled to body 11 upon deformable material 14 being transitioned to a non-deformable state. In certain embodiments, prior to applying orientation structure 14, one or more additional openings may be made in body 11, the one or more additional openings functioning to improve the coupling between orientation structure 14 and body 11.

At step 106, fitting 16 may attached to body 11, if appropriate. In certain embodiments, prior to attaching fitting 16, an opening may need to be made in body 11 through which gases may flow. In certain embodiments, body 11 may initially include an existing fitting positioned in proximity to the location where orientation structure 14 will be applied. In these embodiments, it may be advantageous to remove the existing fitting. In certain embodiments, an opening in body 11 corresponding to the location of the existing fitting may be utilized as opening 18.

Although an example method is described, the steps may be accomplished in any appropriate order. For example, fitting 16 may be attached to body 11 prior to or subsequent to orientation structure 14 being coupled to body 11. The present invention contemplates using methods with additional steps, fewer steps, or different steps, so long as the methods remain appropriate for orienting medical mask 10 to an oral appliance.

Figure 4:
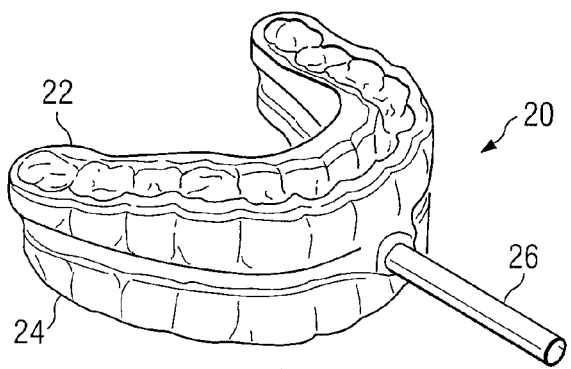
FIG. 4 illustrates an example oral appliance.

FIG. 4 illustrates an example oral appliance 20 for use with medical mask 10. In certain embodiments, oral appliance 20 includes upper arch 22, lower arch 24, and post 26. In alternative embodiments, oral appliance 20 may include post 26 and only one of upper arch 22 and lower arch 24. Upper arch 22 may be configured to receive a user's upper teeth. Lower arch 24 may be configured to receive a user's lower teeth. As used herein, reference to a user's teeth is meant to include any one or more of the user's teeth depending on the structure of the oral appliance. In certain embodiments, oral appliance 20 may be custom-made to fit the unique dental structure of a particular user. In alternative embodiments, oral appliance 20 may be made as a non-custom oral appliance that may or may not be transformed from a non-custom oral appliance to a custom oral appliance. For example, oral appliance 20 may be a "boil-and-bite" type device that includes a thermoplastic material that may be heated and customized for a particular user.

In certain embodiments, oral appliance 20 includes one or more structures or materials configured to couple upper arch 22 to lower arch 24. For example, these one or more structures or materials may be configured to position lower arch 24 relative to upper arch 22 to define a particular position for the user's lower jaw relative to the user's upper jaw. In particular embodiments, oral appliance 20 may include one or more structures to adjustably couple upper arch 22 to lower arch 24. In certain embodiments, upper arch 22 and lower arch 24 may be combined in a single integrated structure. In certain embodiments, oral appliance 20 may represent a bite register or wax mold suitable to receive either or both of the particular user's upper and lower teeth.

In certain embodiments, post 26 may represent one or more structures configured to project out of the user's mouth when oral appliance 20 is positioned in the user's mouth. Although post 26 may have any suitable shape, in a particular embodiment, post 26 may represent a substantially straight, cylindrical projection that may be greater than one inch in length. Post 26 may have a substantially circular or any other suitable cross-section. For example, in a particular embodiment, post 26 may have an elliptical cross section, or other non-circular cross-section, to define a particular rotational orientation between oral appliance 20 and medical mask 10. In certain embodiments, post 26 may be removable from oral appliance 20. Example embodiments of oral appliance 20 that may be used with medical mask 10 are described, for example, in U.S. Pat. Nos. 5,954,048; 5,983,892; 6,209,542; 6,374,824; 6,405,729; and 6,571,798.

Figure 5A:
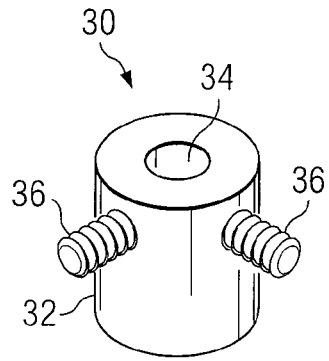
FIGS. 5A through 5C illustrate example locking mechanisms.
Figure 5B:
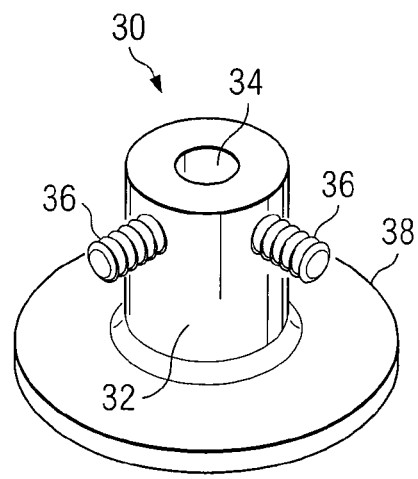
Figure 5C:
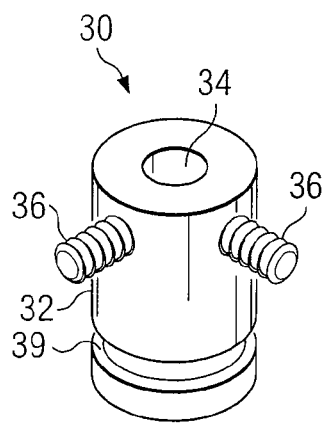

FIGS. 5A through 5C illustrate example locking mechanisms 30 for use with orientation structure 14 of medical mask 10. Locking mechanism 30 may represent one or more structures configured to receive and secure post 26 of oral appliance 20. In certain embodiments, locking mechanism 30 may include sleeve 32 with an opening 34 configured to receive post 26 of oral appliance 20. Locking mechanism 30 may further include one or more threaded openings configured to receive one or more set screws 36 to secure post 26 of oral appliance 20 within locking mechanism 30.

As shown in FIG. 5B, in certain embodiments, locking mechanism 30 may include one or more flanges 38. In certain embodiments, the use of one or more flanges 38 may provide additional structural support or stability for locking mechanism 30. For example, the use of one or more flanges 38 may assist in distributing both linear and angular forces across a broader area to stabilize locking mechanism 30. In certain embodiments, the use of one or more flanges 38 may provide improved coupling between locking mechanism 30 and deformable material 15 or other components of orientation structure 14. For example, the additional surface area provided by one or more flanges 38 may improve adhesion to deformable material 15. As another example, portions of deformable material 15 may envelop or be applied over portions of the one or more flanges 38 to secure locking mechanism 30.

As shown in FIG. 5C, locking mechanism may include one or more notches 39. In certain embodiments, the use of one or more notches 39 may improve the coupling between locking mechanism 30 and deformable material 15 or one or more other components of orientation structure 14. For example, deformable material may fill all or a portion of the one or more notches 39 to secure locking mechanism 30. In certain embodiments, locking mechanism 30 may include any appropriate combination of one or more flanges 38 and one or more notches 39. Locking mechanism 30 may be formed from an acrylic or other polymer; from aluminum, stainless steel, titanium, or other appropriate metal or alloys thereof; or from any other appropriate material.

Figure 6:
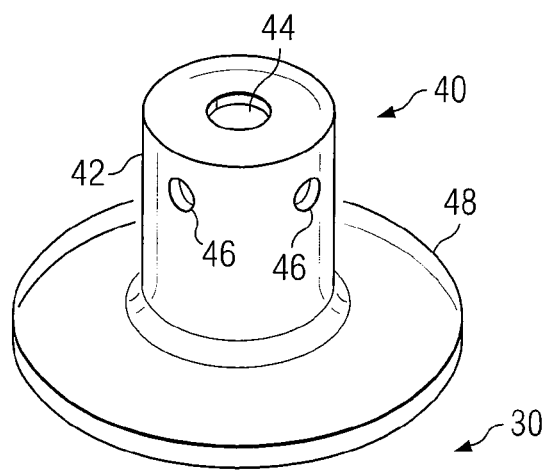
FIG. 6 illustrates an example cover for a locking mechanism.
Figure 6:
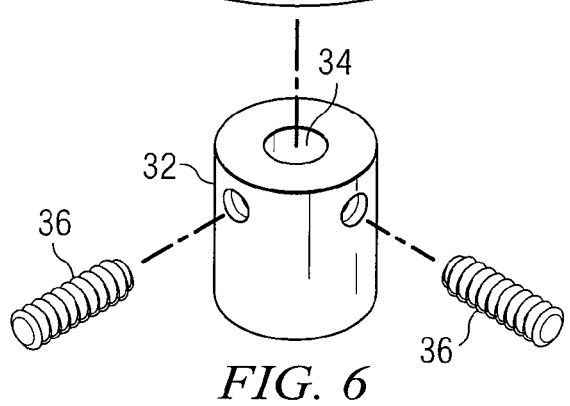

In certain embodiments, in addition to or in lieu of one or more flanges 38 and notches 39, locking mechanism 30 may include cover 40. FIG. 6 illustrates an example cover 40 that may be used with locking mechanism 30. Cover 40 may represent one or more structures configured to be positioned over sleeve 32 to provide additional structural support or improved coupling. In certain embodiments, cover 40 may include housing 42, opening 44, one or more openings 46, and flange 48. In operation, cover 40 may be positioned over sleeve 32 such that openings 46 align with set screws 36 and opening 44 aligns with opening 34. In certain embodiments, flange 48 may provide one or more of the functions discussed above with respect to flange 32 of locking mechanism 30.

Figure 7A:
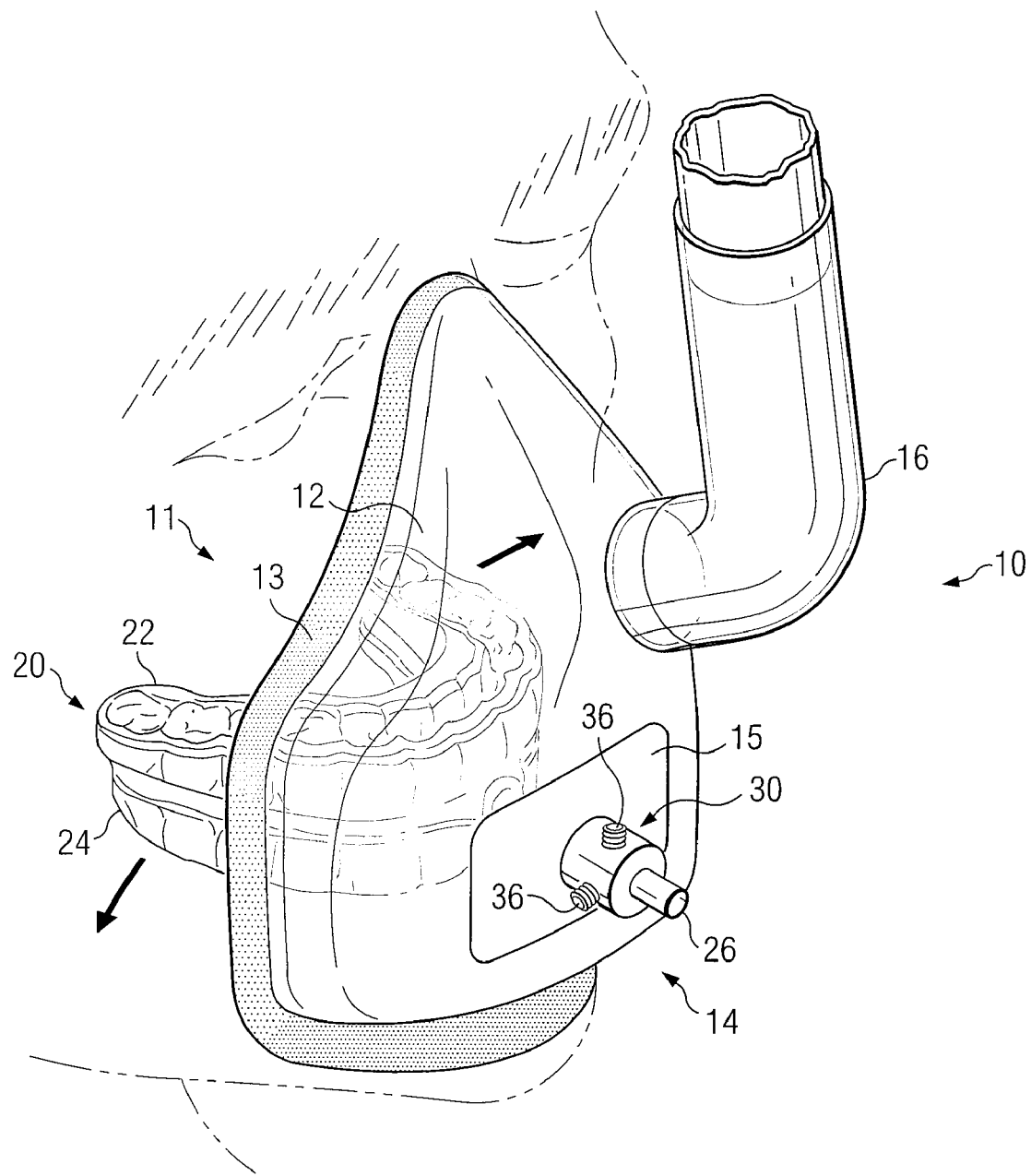
FIGS. 7A and 7B illustrate an example medical mask coupled to an example oral appliance.
Figure 7B:
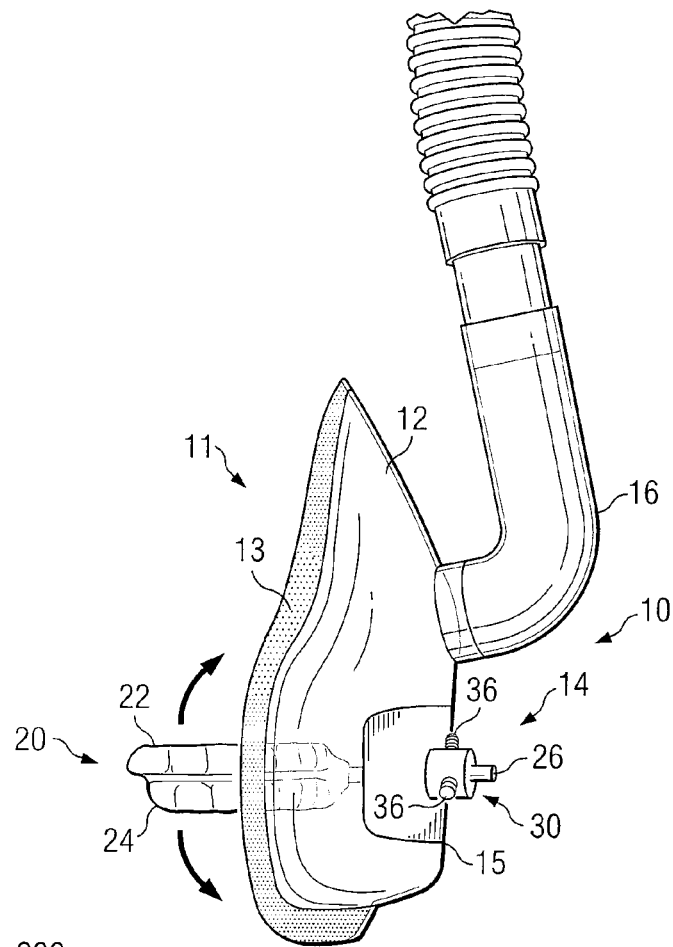

FIGS. 7A and 7B illustrate an example medical mask 10 coupled to an example oral appliance 20. Using orientation structure 14, medical mask 10 may be custom-oriented to a particular user. This custom orientation may be based on the fit of oral appliance 20 relative to the unique dental structure of the particular user, and the established orientation between oral appliance 20 and medical mask 10 provided via post 26 and orientation structure 14. For example, using locking mechanism 30 including one or more set screws 36, the position of medical mask 10 along the axis of post 26 may be fixed. As another example, when deformable material 15 is in a deformable state, the vertical and horizontal positioning of medical mask 10 relative to oral appliance 20 may be allowed to float within a region defined by the size and shape of opening 18 in body 11 relative to the size and shape of post 26. As another example, when deformable material 15 is in a deformable state, the angular orientation of oral appliance 20 relative to medical mask 10 may be allowed to float (as indicated by the arrows in FIGS. 7A and 7B). In these examples, the custom orientation of medical mask 10 relative to oral appliance 20 may be established once set screws 36 are engaged and deformable material 15 is transitioned to a non-deformable state.

Figure 8:
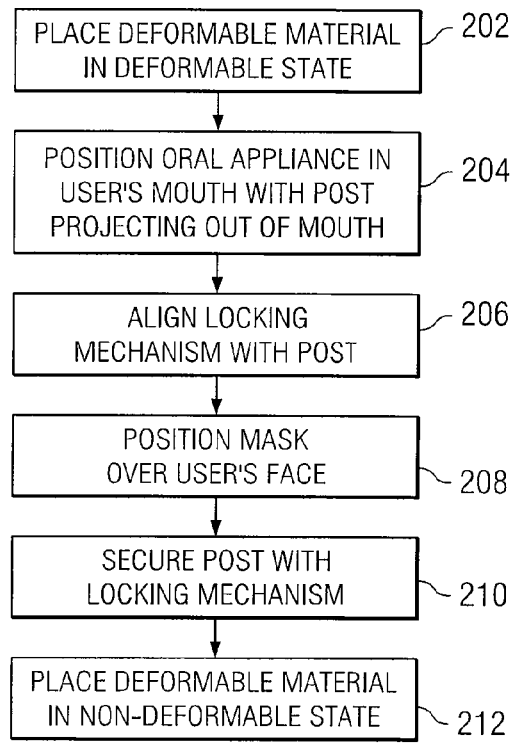
FIG. 8 illustrates an example method for custom-orienting a medical mask to an oral appliance.

FIG. 8 illustrates an example method 200 for custom orienting medical mask 10 to oral appliance 20. At step 202, deformable material 15 is placed in a deformable state. For example, where deformable material 15 includes one or more polycaprolactone polymers, the deformable material may be heated (separately or together with one or more other components of medical mask 10) in a microwave oven, in water or other non-solvent neutral liquid, or in any suitable manner to between approximately 140° F. and approximately 180° F., so as to place deformable material 15 in a deformable state.

At step 204, oral appliance 20 is positioned in a user's mouth with post 26 projecting out of the user's mouth. In embodiments where oral appliance 20 includes upper arch 22 and lower arch 24 adjustably coupled together, the orientation of upper arch 22 relative to lower arch 24 may be adjusted to achieve a desired position of the user's lower jaw. At step 206, locking mechanism 30 is aligned with post 26. For example, opening 34 of locking mechanism 30 may be aligned with the distal tip of post 26 of oral appliance 20. At step 208, medical mask 10 is positioned over the user's face. In certain embodiments, medical mask 10 may be adjusted to achieve a desired comfort level and minimal leakage. At step 210, post 26 is secured using locking mechanism 30. For example, in embodiments of locking mechanism 30 that include set screws 36, post 26 may be secured by tightening set screws 36. At step 212, deformable material 15 is placed in a non-deformable state. For example, in embodiments in which deformable material 15 includes a thermoplastic polymer, such as a polycaprolactone polymer, deformable material 15 may be placed in a non-deformable state by causing or allowing deformable material 15 to cool to room temperature.

Although an example method is described, the steps may be accomplished in any appropriate order and the present invention contemplates using methods with additional steps, fewer steps, or different steps, so long as the methods remain appropriate for orienting a medical mask to an oral appliance. For example, in certain embodiments, deformable material 15 may be provided in a deformable state and thus step 202 may be eliminated. As another example, one or more of steps 202 through 212 may be repeated until a desired fit is achieved between medical mask 10 and the user's unique facial features. As another example, according to an alternative method, oral appliance 20 may be inserted into the user's mouth with post 26 projecting out of the user's mouth, medical mask 10 may be positioned over the user's face, deformable material 15 may be applied to medical mask 10 while in a deformable state, and then deformable material 15 may be transitioned to a non-deformable state. In this example, locking mechanism may be aligned with and secured to post 26 before oral appliance 20 is inserted into the user's mouth, before medical mask 10 is positioned over the user's face, before deformable material 15 is applied to medical mask 10, or after deformable material 15 is applied to medical mask 10.

In certain embodiments, deformable material 15 may include a thermoplastic polymer and body 11 may include a non-thermoplastic polymer, such that when medical mask 10 is heated to transition deformable material 15 to a deformable state, the shape of body 11 will not be substantially affected. In other embodiments, deformable material 15 may include a first thermoplastic polymer and body 11 may include a second thermoplastic polymer, such that the second thermoplastic polymer exhibits thermoplastic behavior at higher temperatures than that of the first thermoplastic polymer. In this alternative embodiment, medical mask 10 may be heated to a temperature range sufficient to transition deformable material 15 to a non-deformable state but insufficient to transition body 12 to a deformable state. In yet other embodiments, body 11 and deformable material 15 may include the same materials. For example, both body 11 and deformable material 15 may be light curable polymers. In this example, body 11 may initially be formed and cured, then deformable material 15 may be applied to body 11 while body 11 is positioned on a user's face, and then deformable material 15 may be cured and transitioned to a non-deformable state.

Although the present invention has been described in several embodiments, a plenitude of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A method of forming a custom-oriented medical mask having a body and an orientation structure, comprising:
    transitioning a deformable material for the orientation structure of the medical mask from a first non-deformable state to a deformable state;
    positioning in a user's mouth an oral appliance having a post, such that the oral appliance receives the user's teeth and the post of the oral appliance projects out of the user's mouth;
    positioning the medical mask over the user's face, such that:
        the body of the medical mask covers portions of the user's face including at least the user's mouth and a portion of the user's nose surrounding the user's nostrils;
        the body of the medical mask contacts the user's face surrounding the covered portions of the user's face and substantially prevents gas from escaping between the body and the contacted portions of the user's face; and
        the post of the oral appliance is received in the orientation structure of the medical mask to establish a custom orientation between the medical mask and the post of the oral appliance; and
    while the post of the oral appliance is received in the orientation structure of the medical mask, allowing the deformable material to transition from the deformable state to a second non-deformable state, such that the custom orientation between the medical mask and the post of the oral appliance is maintained.

2. The method of claim 1, wherein the body of the medical mask comprises a tray configured to receive at least a portion of the orientation structure to position the orientation structure relative to the body of the medical mask.

3. The method of claim 1, wherein the body of the medical mask comprises a sealing portion configured to contact the user's face surrounding the covered portions of the user's face to substantially prevent gas from escaping between the body of the medical mask and the contacted portions of the user's face.

4. The method of claim 1, wherein the body comprises a first polymer and the deformable material comprises a second polymer different from the first polymer.

5. The method of claim 1, wherein the body comprises a thermosetting polymer and the deformable material comprises a thermoplastic polymer.

6. The method of claim 1, wherein the deformable material comprises a polycaprolactone polymer.

7. The method of claim 1, wherein the orientation structure of the medical mask comprises a locking mechanism coupled to the deformable material.

8. The method of claim 7, further comprising securing the post of the oral appliance within the locking mechanism of the orientation portion while the post of the oral appliance is received within the locking mechanism.

9. The method of claim 1, further comprising coupling a fitting to the body, the fitting configured to couple the medical mask to a clinical gas delivery system.

10. A medical mask, comprising:
    a body comprising a first polymer and configured to:
        cover portions of a user's face comprising the user's mouth and at least portions of the user's nose comprising the nostrils; and
        contact the user's face surrounding the covered portions of the user's face to substantially prevent gas from escaping between the body and the contacted portions of the user's face; and
    an orientation structure configured to receive an oral appliance post to establish and maintain a custom orientation between the medical mask and the oral appliance post, the orientation structure comprising a deformable material comprising a second polymer capable of transitioning between deformable and non-deformable states.

11. The medical mask of claim 10, wherein the body further comprises a tray configured to receive at least a portion of the orientation structure to position the orientation structure relative to the body.

12. The medical mask of claim 10, wherein the body further comprises a sealing portion configured to contact the user's face surrounding the covered portions of the user's face to substantially prevent gas from escaping between the body and the contacted portions of the user's face.

13. The medical mask of claim 10, wherein the first polymer is a thermosetting polymer and the second polymer is a thermoplastic polymer.

14. The medical mask of claim 10, wherein the second polymer is a polycaprolactone polymer.

15. The medical mask of claim 10, further comprising a locking mechanism coupled to the deformable material and configured to receive and secure an oral appliance post.

16. The medical mask of claim 10, further comprising a fitting configured to couple the medical mask to a clinical gas delivery system.

17. A medical mask, comprising:
- a body comprising a non-thermoplastic polymer and configured to:
  - cover portions of a user's face comprising the user's mouth and at least portions of the user's nose comprising the nostrils; and
  - contact the user's face surrounding the covered portions of the user's face to substantially prevent gas from escaping between the body and the contacted portions of the user's face;
- an orientation structure configured to establish and maintain a custom orientation between the medical mask and a post of an oral appliance, the orientation structure comprising:
- a thermoplastic polymer; and
- a locking mechanism coupled to the thermoplastic polymer and configured to receive and secure a post of an oral appliance; and
- a fitting configured to couple the medical mask to a clinical gas delivery system.

18. The medical mask of claim 17, wherein the body further comprises a tray configured to receive at least a portion of the orientation structure to position the orientation structure relative to the body.

19. The medical mask of claim 17, wherein the body further comprises:
- a shell comprising the non-thermoplastic polymer and configured to cover portions of the user's face and direct a gas to the user; and
- a sealing portion configured to contact the user's face surrounding the covered portions to substantially prevent the gas from escaping between the shell and the contacted portions of the user's face.

20. The medical mask of claim 17, wherein the thermoplastic polymer is a polycaprolactone polymer.

* * * * *